(12) United States Patent  
Ein-Gal

(10) Patent No.: US 6,210,314 B1
(45) Date of Patent: Apr. 3, 2001

(54) PROSTATE RADIOTHERAPY APPARATUS

(76) Inventor: Moshe Ein-Gal, Azar Street 30, 47203 Ramat Hasharon (IL)

( * ) Notice: Subject to any disclaimer, the term of this patent is extended or adjusted under 35 U.S.C. 154(b) by 0 days.

(21) Appl. No.: 09/308,087

(22) PCT Filed: Sep. 28, 1998

(86) PCT No.: PCT/IL98/00472
§ 371 Date: Jul. 6, 1999
§ 102(e) Date: Jul. 6, 1999

(87) PCT Pub. No.: WO99/16507
PCT Pub. Date: Apr. 8, 1999

(30) Foreign Application Priority Data

Sep. 29, 1997 (IL) ........................................................ 121861

(51) Int. Cl.[7] ................. A61N 5/00; A61B 5/05
(52) U.S. Cl. ................ 600/3; 600/427; 607/96; 607/101
(58) Field of Search .................. 600/1–7, 411, 600/427, 439; 607/96, 101

(56) References Cited

U.S. PATENT DOCUMENTS

| 5,234,004 | * | 8/1993 | Hascoet et al. ........................ 607/116 |
| 5,385,544 | * | 1/1995 | Edwards et al. ........................ 604/22 |
| 5,472,405 | * | 12/1995 | Buchholtz et al. ....................... 601/2 |
| 5,474,071 | | 12/1995 | Chapelon . |
| 5,480,417 | | 1/1996 | Hascoet . |
| 5,509,929 | | 4/1996 | Hascoet . |
| 5,599,294 | | 2/1997 | Edwards . |
| 5,759,162 | * | 6/1998 | Oppelt et al. ............................ 601/2 |

\* cited by examiner

Primary Examiner—Samuel G. Gilbert
(74) Attorney, Agent, or Firm—Welsh & Katz, Ltd.

(57) ABSTRACT

Radiotherapy apparatus including a first probe insertable into a first body cavity, a second probe insertable into a second body cavity, and an external frame attached to the first and the second probes, such that the first and the second probes are in a fixed, known spatial relationship with respect to the external frame.

13 Claims, 1 Drawing Sheet

PROSTATE RADIOTHERAPY APPARATUS

FIELD OF THE INVENTION

The present invention relates to prostate radiotherapy generally, and particularly to apparatus for spatially fixing a target volume in a prostate which is to be irradiated.

BACKGROUND OF THE INVENTION

The use of radiotherapy to render tissue necrotic is well established, especially in treatment of tumors. A target volume in the tissue is irradiated at a multiplicity of orientations with finely collimated beams. A particular form of radiotherapy, called stereotactic radiotherapy, requires precise localization and fixation of the target tissue. It is essential to rigidly fix the target volume in space in order to ensure that the radiation beams are correctly directed to the target. However, it is difficult, impractical and sometimes impossible to rigidly fix some limbs in the human body sufficiently for precise stereotactic radiotherapy. The head is basically the only human organ wherein the bone is so close to the skin and accessible so as to permit rigorously spatially fixing the cranium to a stereotactic frame.

It is readily understood that it is quite desirable to rigidly fix other organs, such as the prostate, to permit stereotactic radiotherapy. However, the prior art does not have any method or apparatus for spatially fixing the prostate.

SUMMARY OF THE INVENTION

The present invention seeks to provide apparatus for spatially fixing a target volume in a prostate which is to be irradiated. The present invention also provides safety features such as injection of water in the area of Denonvilliers' fascia for reflecting the rectal wall away from the prostate and provision of cooling in the area of the prostate to reduce the adverse effects of radiation on healthy tissue, e.g., the rectal wall or urethra.

Although the present invention will be described herein with reference to prostate radiotherapy, it is understood that the present invention is applicable to radiotherapy of other organs in males or females wherein two probes can be inserted into the body for fixing therein an organ for stereotactic radiotherapy.

There is thus provided in accordance with a preferred embodiment of the present invention radiotherapy apparatus including a first probe insertable into a first body cavity, a second probe insertable into a second body cavity, and an external frame attached to the first and the second probes, such that the first and the second probes are in a fixed, known spatial relationship with respect to the external frame.

In accordance with a preferred embodiment of the present invention the first probe includes a urethral probe insertable into a urethra and the second probe includes a rectal probe insertable into a rectum.

Further in accordance with a preferred embodiment of the present invention the radiotherapy apparatus includes a source of radiation which produces a radiation beam, having a fixed, known spatial relationship with respect to the external frame, that irradiates a target substantially spatially fixed by the first and the second probes.

Still further in accordance with a preferred embodiment of the present invention the radiation beam exits a distal end of at least one of the first probe and the second probe. The radiation may be infrared (IR) radiation, microwave radiation, gamma ray radiation, or radio frequency (RF) electrical energy.

Additionally in accordance with a preferred embodiment of the present invention the radiotherapy apparatus includes adjustment apparatus that adjusts the spatial relationship of the first and the second probes with respect to the external frame.

Further in accordance with a preferred embodiment of the present invention the radiotherapy apparatus includes a beam controller for controlling an intensity of the radiation beam.

Additionally in accordance with a preferred embodiment of the present invention the radiotherapy apparatus includes imaging apparatus that determines a position of the target with reference to the external frame.

In accordance with a preferred embodiment of the present invention imaging energy of the imaging apparatus is directed through a distal end of at least one of the first probe and the second probe. The imaging apparatus may comprise ultrasound apparatus.

Further in accordance with a preferred embodiment of the present invention the radiotherapy apparatus includes cooling apparatus that cools tissue adjacent to at least one of the first probe and the second probe.

In accordance with a preferred embodiment of the present invention at least one of the first and the second probes comprises an electrode for delivering electrical current.

Further in accordance with a preferred embodiment of the present invention there is provided injection apparatus for injecting a fluid in the vicinity of Denonvilliers' fascia to reflect a rectal wall from a prostate.

BRIEF DESCRIPTION OF THE DRAWINGS

The present invention will be understood and appreciated more fully from the following detailed description, taken in conjunction with the drawing in which.

DETAILED DESCRIPTION OF PREFERRED EMBODIMENTS

Figure 1:
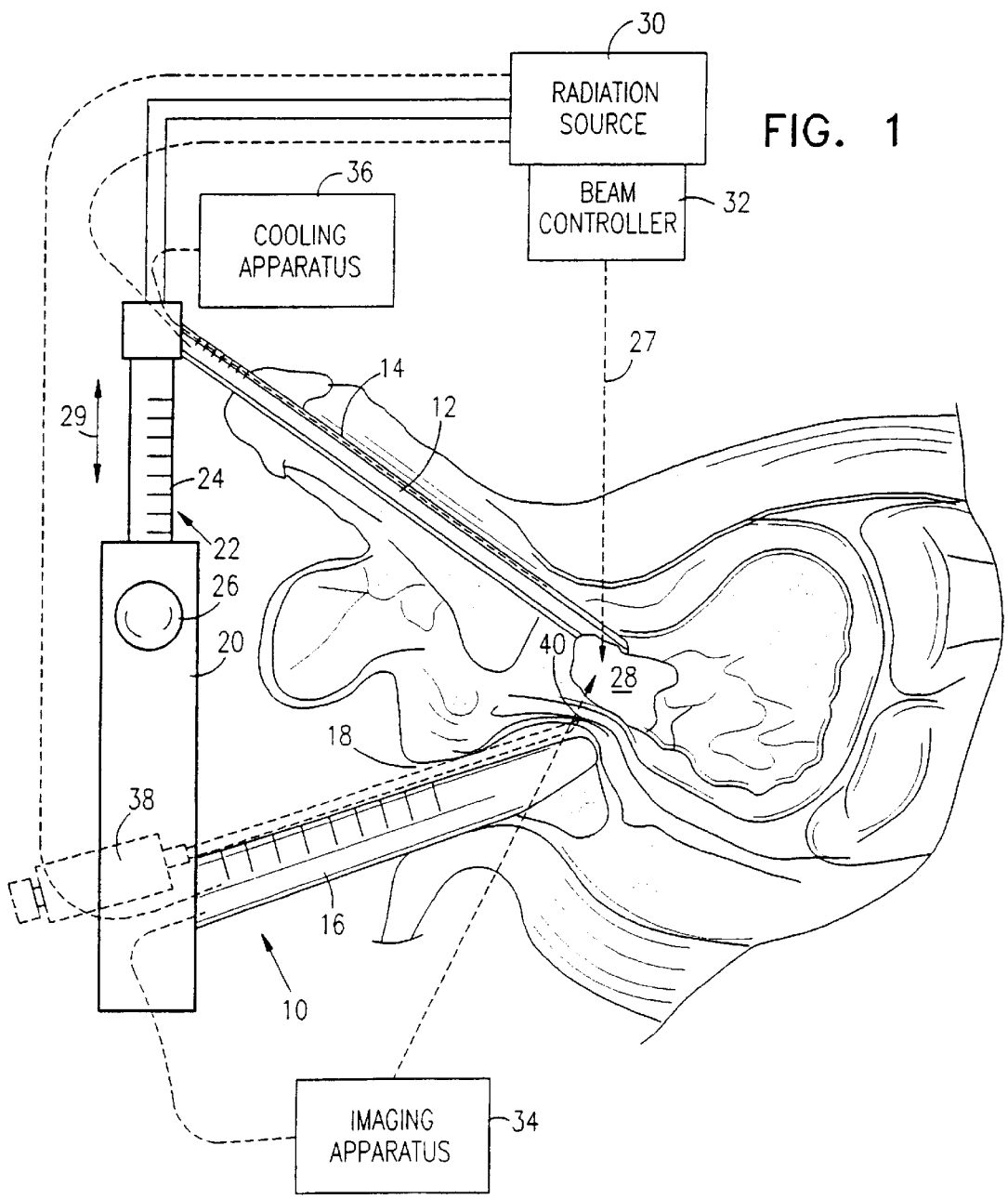
FIG. 1 is a simplified pictorial illustration of radiotherapy apparatus constructed and operative in accordance with a preferred embodiment of the present invention.

Reference is now made to FIG. 1 which illustrates radiotherapy apparatus 10 constructed and operative in accordance with a preferred embodiment of the present invention.

Radiotherapy apparatus 10 includes a first probe 12 insertable into a first body cavity 14, and a second probe 16 insertable into a second body cavity 18. As mentioned above, the present invention is described herein with reference to prostate radiotherapy, and thus first probe 12 is herein referred to as a urethral probe 12 and first body cavity 14 is referred to as a urethra 14. Second probe 16 is herein referred to as a rectal probe 16 and second body cavity 18 is referred to as a rectum 18.

An external frame 20 is attached to urethral probe 12 and rectal probe 16, such that probes 12 and 16 are in a fixed spatial relationship with respect to external frame 20. External frame 20 preferably includes adjustment apparatus 22 that adjusts the spatial relationship of urethral probe 12 and rectal probe 16 with respect to external frame 20. For example, adjustment apparatus 22 may include a slidable, graduated rod 24 that is attached to urethral probe 12 and an adjustment knob 26. Rod 24 may be lowered or raised generally along an axis 29 and tightened at a fixed position by means of knob 26.

A source 30 of radiation, such as infrared (IR) radiation, microwave radiation, gamma ray radiation, radio frequency (RF) electrical energy, depending on the type of therapy, for example, produces a radiation beam 27 that irradiates a target 28, such as a prostate. In one preferred embodiment, source 30 is an external source fixed relative to external frame 20. Alternatively, radiation beam 27 may be suitably guided to exit a distal end of either one of the probes 12 or 16. In any case, radiation beam 27 has a fixed, known spatial relationship with respect to external frame 20, and radiation beam 27 irradiates target 28 which is substantially spatially fixed by probes 12 and 16. A beam controller 32 is preferably provided for controlling an intensity of radiation beam 27.

In accordance with another preferred embodiment of the present invention one or both of probes 12 and 16 comprises an electrode for delivering electrical current to target 28.

Imaging apparatus 34 is preferably provided for producing an image of target 28 and for tracking and monitoring the progress of the treatment procedure. Imaging apparatus 34 determines the position of target 28 with reference to external frame 20 so that radiation beam 27, whose position is also fixed relative to external frame 20, may be accurately aimed at target 28. Imaging apparatus 34 may be a fluoroscope, X-ray machine or ultrasound imaging equipment, for example. In one preferred embodiment, imaging apparatus 34 is located externally to probes 12 and 16. Alternatively, imaging energy of imaging apparatus 34 may be directed through the distal ends of either or both probes 12 and 16.

Cooling apparatus 36 is preferably provided for cooling one or both probes 12 and 16. Cooling apparatus 36 may include cooling coils that transport a refrigerant fluid along a length of the probes. Alternatively, cooling apparatus 36 may include thermoelectric coolers that work on the Peltier effect, such as units commercially available from Melcor, Inc. USA. The provision of cooling apparatus 36 is particularly important if radiation beam 27 is transmitted through one of probes 12 or 16, since the radiation beam tends to heat the area through which it passes, and this heat may be detrimental to delicate healthy tissues in the vicinity of the probes.

As an added safety feature, injection apparatus 38 may be provided for injecting a fluid, such as water, through the perineum to the vicinity of Denonvilliers' fascia, reference numeral 40, to reflect the rectal wall from the prostate. It is believed that the fluid does not affect the spatial fixation of the prostate by probes 12 and 16.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. Radiotherapy apparatus comprising:

a first probe insertable into a first body cavity;

a second probe insertable into a second body cavity;

an external frame attached to said first and said second probes, such that said first and said second probes are in a fixed, known spatial relationship with respect to said external frame and maintain a target organ in a fixed, known spatial relationship with respect to said external frame; and a source of radiation fixed with respect to said external frame and which produces a radiation beam directed to said target organ.

2. Radiotherapy apparatus according to claim 1 wherein said first probe comprises a urethral probe insertable into a urethra, and said second probe comprises a rectal probe insertable into a rectum.

3. Radiotherapy apparatus (10) according to claim 1 and further comprising a source (30) of radiation which produces a radiation beam (27), having a fixed, known spatial relationship with respect to said external frame (20), that irradiates a target (28) substantially spatially fixed by said first (12) and said second (16) probes.

4. Radiotherapy apparatus according to claim 1 and wherein said radiation beam exits a distal end of at least one of said first probe and said second probe.

5. Radiotherapy apparatus according to claim 1 and wherein said radiation is selected from the group consisting of: infrared (IR) radiation, microwave radiation, gamma ray radiation, and radio frequency (RF) electrical energy.

6. Radiotherapy apparatus according to claim 1 and comprising adjustment apparatus that adjusts the spatial relationship of said first and said second probes with respect to said external frame.

7. Radiotherapy apparatus according to claim 1 and comprising a beam controller for controlling an intensity of said radiation beam.

8. Radiotherapy apparatus according to claim 1 and comprising imaging apparatus that determines a position of said target with reference to said external frame.

9. Radiotherapy apparatus according to claim 8 and wherein imaging energy of said imaging apparatus is directed through a distal end of at least one of said first probe and said second probe.

10. Radiotherapy apparatus according to claim 8 and wherein said imaging apparatus comprises ultrasound apparatus.

11. Radiotherapy apparatus according to claim 1 and comprising cooling apparatus that cools tissue adjacent to at least one of said first probe and said second probe.

12. Radiotherapy apparatus according to claim 1 and wherein at least one of said first and said second probes comprises an electrode for delivering electrical current.

13. Radiotherapy apparatus according to claim 1 and comprising injection apparatus for injecting a fluid in the vicinity of Denonvilliers' fascia to reflect a rectal wall from a prostate.

* * * * *